(12) United States Patent
Kang et al.

(10) Patent No.: US 11,464,649 B2
(45) Date of Patent: Oct. 11, 2022

(54) EXPANDABLE SPINAL FUSION CAGE

(71) Applicant: L&K BIOMED CO., LTD., Yongin-si (KR)

(72) Inventors: Gook Jin Kang, Seoul (KR); Youngbo Ahn, Irvine, CA (US); Sang Soo Lee, Anyang-si (KR); Sun Kak Choi, Gwangju-si (KR)

(73) Assignee: L&K BIOMED CO., LTD., Yongin-si (KR)

( * ) Notice: Subject to any disclaimer, the term of this patent is extended or adjusted under 35 U.S.C. 154(b) by 0 days.

(21) Appl. No.: 16/632,419

(22) PCT Filed: Nov. 12, 2019

(86) PCT No.: PCT/KR2019/015339
§ 371 (c)(1),
(2) Date: Jan. 20, 2020

(87) PCT Pub. No.: WO2021/049711
PCT Pub. Date: Mar. 18, 2021

(65) Prior Publication Data
US 2021/0259848 A1    Aug. 26, 2021

(30) Foreign Application Priority Data

Sep. 11, 2019 (KR) .......................... 10-2019-0112746

(51) Int. Cl.
*A61F 2/44* (2006.01)
*A61F 2/30* (2006.01)

(52) U.S. Cl.
CPC .......... *A61F 2/447* (2013.01); *A61F 2/30771* (2013.01); *A61F 2/4425* (2013.01); *A61F 2002/3055* (2013.01); *A61F 2002/30878* (2013.01); *A61F 2002/443* (2013.01)

(58) Field of Classification Search
CPC ................ A61F 2/30771; A61F 2/4425; A61F 2002/3055; A61F 2002/30878; A61F 2002/443; A61F 2/4455–2/447; A61F 2002/30556; A61F 2002/30579; A61F 2250/0048; A61F 2250/0009
See application file for complete search history.

(56) References Cited

U.S. PATENT DOCUMENTS

| | | | |
|---|---|---|---|
| 8,894,711 B2 * | 11/2014 | Varela | A61F 2/4611 623/17.16 |
| 10,219,915 B1 * | 3/2019 | Stein | A61F 2/447 |
| 10,278,830 B1 * | 5/2019 | Walker | A61F 2/4455 |

(Continued)

*Primary Examiner* — Julianna N Harvey
(74) *Attorney, Agent, or Firm* — WHDA, LLP

(57) ABSTRACT

The present invention provides a spinal fusion cage that can be inserted between vertebral bodies at the lowest height, and the height thereof may be adjusted with being inserted, such that cages having different heights within a certain range may be replaced by one cage. Therefore, the number of product groups that should be produced is reduced and the amount in stock is also decreased on the manufacturer. In addition, unlike the cage having a predetermined height at a constant interval in the prior art, the height of the spinal fusion cage is linearly adjusted according to a spacing between vertebral bodies of a patient, such that the surgery may be performed at the optimal height according to spinal conditions of the patient.

7 Claims, 13 Drawing Sheets

(56) References Cited

U.S. PATENT DOCUMENTS

| | | | |
|---|---|---|---|
| 10,993,814 B2* | 5/2021 | Wolters | A61F 2/442 |
| 2008/0140207 A1* | 6/2008 | Olmos | A01H 5/12 |
| | | | 623/17.16 |
| 2010/0211176 A1* | 8/2010 | Greenhalgh | A61F 2/447 |
| | | | 623/17.15 |
| 2011/0282453 A1* | 11/2011 | Greenhalgh | A61F 2/4425 |
| | | | 623/17.16 |
| 2014/0257484 A1* | 9/2014 | Flower | A61F 2/447 |
| | | | 29/460 |
| 2017/0151065 A1* | 6/2017 | Warren | A61F 2/4601 |
| 2017/0224505 A1* | 8/2017 | Butler | A61F 2/447 |
| 2018/0193160 A1* | 7/2018 | Hsu | A61F 2/447 |
| 2019/0262139 A1* | 8/2019 | Wolters | A61F 2/447 |
| 2019/0307577 A1* | 10/2019 | Predick | A61F 2/4455 |

* cited by examiner

EXPANDABLE SPINAL FUSION CAGE

TECHNICAL FIELD

The present invention relates to an expandable spinal fusion cage, and more specifically, to a spinal fusion cage that can be inserted between vertebral bodies at the lowest height, and the height thereof may be adjusted with being inserted.

BACKGROUND ART

A vertebral body includes 32 to 35 vertebrae forming a body, and intervertebral disks, i.e., spinal disks arranged between the vertebrae, and is a portion forming a backbone of a human body that connects an upper skull and a lower pelvis to form the pillar of the truncus.

The spine includes 7 cervical vertebrae, 12 thoracic vertebrae, 5 lumbar vertebrae, 5 sacral vertebrae, and 3 to 5 coccyges from the top. In the case of an adult, 5 sacral vertebrae are fused together to form one sacral vertebra, and 3 to 5 coccyges are fused together to form one tailbone.

As one of the treatment methods for treating serious spinal diseases for a long time, there is spinal fusion. Such spinal fusion is a surgical method which includes removing an intervertebral disc, and inserting a cage that replaces the intervertebral disc to fuse adjacent vertebral bodies to each other.

When performing the spinal fusion in the lumbar vertebrae, it may be divided into posterior lumbar interbody fusion (PLIF), transforaminal lumbar interbody fusion (TLIF), direct lateral lumbar interbody fusion (DLIF), oblique lumbar interbody fusion (OLIF), and anterior lumbar interbody fusion (ALIF) depending on an insertion direction of the cage.

The PLIF is a method which includes incising a back along a centerline of the spine, opening so as to expose all of the vertebral bodies, removing a portion of the posterior side of the vertebra, then removing the disc, and inserting a PLIF cage between the vertebrae.

The PLIF has been performed from the oldest among the spinal fusions, and is an absolutely necessary method when fusing two or three joints. However, due to a surgical process, the PLIF has various disadvantages such as high possibility of adhesion to nerves, ligaments and muscles, extended period of time for a healing time due to a large incision area, and great aftereffects for some people.

The PLIF cage is the smallest of the cages used in all spinal fusions, wherein a pair of small cages are displaced on left and right sides of the spine.

The TLIF is a surgical method which includes incising the back in a small area along both sides of a spinal muscle, exposing the vertebral bodies to a minimum, and then inserting the TLIF cage by replacing the disc while removing a spinal joint site in a direction coming out of a neuropore. This surgical technique is suitable for a case of one joint due to advantages of less bleeding, and reduced operation time. However, if an operation over multiple sites is required, the PLIF surgery should be performed. Most of the TLIF cage is formed in an arch shape, such that it is placed in the vertebral bodies and rotated so that a convex portion of the TLIF cage faces a stomach. The TLIF cage is larger than the PLIF cage, but a support area is smaller than a DLIF cage or ALIF cage which will be described below.

The ALIF has various advantages, such as fast recovery from the operation and no need to worry about adhesions. However, the ALIF has a disadvantage that highly advanced skill is needed because the operation is performed by incising an anterior (stomach) to bypass intestines, and approaching the spine. The ALIF cage has an advantage of having the largest support area among all spinal fusion cages.

The LLIF was developed to overcome the disadvantages of the ALIF, PLIF, and TLIF. Since the operation is performed through flank incision, the LLIF has advantages that an interval of stenosed sites between the vertebrae may be more greatly widened than the conventional surgeries performed by incision of the back, and there is almost no damage to surrounding tissues. However, since a psoas muscle and peritoneum are arranged around a route to be operated, there is a problem of causing thigh muscle paralysis if there is a mistake during the operation. The DLIF cage is smaller than the ALIF cage, but larger than the PLIF cage or TLIF cage.

Compared to the LLIF, the safer and more effective method is the OLIF (it can be called by ATP). The OLIF has advantages that the operation route is formed in a direction inclined from the flank, and the operation is possible between the fourth lumbar vertebra (L4) and the 5th lumbar vertebra (L5), which are difficult to operate by the DLIF due to the psoas muscle and peritoneum. In addition, the possibility of damaging the nerves, which may be a problem in the DLIF, is significantly less.

Conventional spinal fusion cages are made of a single body with no change in cross-sectional area or height using a metallic material such as titanium or a polymeric material such as PEEK. Because of this, it has a large number of products in consideration of the patient's physique, height, race, sex, etc. In other words, the manufacturer has a burden to combine the three variables of width, length and height to produce at least tens to hundreds of products.

In addition, the interval between the vertebra of the patient does not increase at regular intervals, but if produced in a single group, because it is necessary to select the appropriate height from the already existing product range, there is a problem that cannot properly cope with each patient.

Various attempts have been made to solve the above-described problems, and a height adjustable spinal fusion cage has been developed.

U.S. Pat. No. 6,176,882 discloses such a height adjustable cage. The cage of U.S. Pat. No. 6,176,882 includes a rectangular box-shaped wall whose top and bottom are opened, engagement members which move vertically inside the wall, a pair of wedge members for pressing the engagement member, and an adjusting element which is screwed with the wedge members to adjust a spacing of the pair of wedge members. Therefore, U.S. Pat. No. 6,176,882 has a problem that the engagement members and the wedge members are only blocked by the box-shaped wall, and they are not connected to each other, such that the engagement members are shaken.

For comparison, U.S. Pat. No. 9,034,041 discloses, in an invention of claim 1 thereof, a cage generally including a body assembly, an upper support member 718 (hereinafter, not illustrated), and a lower support member 720, wherein the body assembly has a first portion 712 and a second portion 714, and the first portion 712 and the second portion 714 move on a longitudinal axis by a control member. The spacing between the upper support member 718 and the lower support member 720 is defined by a pair of first upper retaining members and a pair of second upper retaining members. Therefore, U.S. Pat. No. 9,034,041 has a problem that the cage does not include a component for directly guiding the mutual movement of the upper support member 718 and the lower support member 720, thus the body assembly, the upper support member 718 and the lower support member 720 are shaken with respect to each other.

US2017-02580605A discloses a holder 400 for a height adjustable cage as illustrated in FIGS. 26 to 29 thereof. US2017-02580605A uses a method in which, a plurality of arms 402 (hereinafter, not illustrated) are inserted into or protrude from a sleeve 410, then protrusions 404 formed on ends of the arms 402 are mounted in grooves 320 of a cage 300 to fix the cage 300. However, such a method has a problem that, since the arm 402 is extended by an elasticity thereof, there is a high possibility that the holder 400 may not be separated with being coupled to an implant 302 due to repeated use or obstruction of surrounding muscles at the surgical site.

PRIOR ART DOCUMENT

Patent Document (Patent Document 1) U.S. Pat. No. 6,176,882
(Patent Document 2) U.S. Pat. No. 9,034,041
(Patent Document 3) U.S. Patent Application Publication No. US2017-02580605A

SUMMARY OF INVENTION

Problems to be Solved by Invention

An object of the present invention is to provide an expandable spinal fusion cage that is inserted between vertebral bodies at the lowest height, and may stably support the movement of a pair of endplates while being able to adjust a height thereof with being inserted.

Means for Solving Problems

To achieve the above object, according to an aspect of the present invention, there is provided a spinal fusion cage including: a first endplate and a second endplate configured to abut adjacent vertebral bodies; a distal moving block installed to relatively move with respect to plate inclined portions formed at one end of each of the first endplate and the second endplate; a proximal moving block installed to relatively move with respect to plate inclined portions formed at the other end of each of the first endplate and the second endplate; an adjusting member rotatably mounted in the proximal moving block and screwed with the distal moving block, so as to adjust a distance between the distal moving block and the proximal moving block; a first guide unit formed in the first endplate toward the second endplate; and a second guide unit formed in the second endplate toward the first endplate to block movements of the first endplate and the second endplate in directions in which they are close to or spaced apart from each other by sliding with the first guide unit, wherein the first guide unit and the second guide unit are configured to support loads of the first endplate and the second endplate in a longitudinal or width direction thereof.

The distal moving block and the proximal moving block may have block sliders formed therein, and the plate inclined portions of the first and second endplates may have plate sliders formed therein to slide with respect to the block sliders.

The block slider and the plate slider may have a shape of a dovetail so as to maintain a state of being engaged with each other.

The adjusting member may include: a threaded portion screwed to a threaded hole formed in the distal moving block at one end; and a pin seat fixed to the other end so as to be rotatable with respect to the proximal moving block, wherein an adjusting member pin is located in the pin seat through the proximal moving block.

The first guide unit may include columns that protrude toward the second endplate, and the second guide unit may include extension walls that extend toward the first endplate to slide with respect to the columns.

The first guide unit may include receiving recesses formed around the columns to receive the extension walls when the first endplate and the second endplate are close to each other.

The extension wall may include: a first wall and a second wall located at a front end and a rear end of the column in the longitudinal direction of the second endplate; and a third wall which connects the first wall and the second wall to form a groove into which the column is inserted.

The first wall and the second wall may have stoppers formed thereon to abut on a bottom surface of the first endplate around the receiving recess, such that the first endplate and the second endplate are spaced apart from each other at a predetermined distance in a state in which the first endplate and the second endplate are maximally close to each other.

The first wall and the second wall may include guide grooves formed therein to guide the column to be inserted into the recess.

The column may be formed so as to have a widthwise thickness greater than ¼ times and smaller than ½ times of a value of excluding a widthwise length of a first window from a widthwise length of a first plate portion.

Advantageous Effects

According to the present invention, cages having different heights within a certain range may be replaced by one cage. Therefore, the number of product groups that should be produced is reduced and the amount in stock is also decreased on the manufacturer. In addition, unlike the cage having a predetermined height at a constant interval in the prior art, the height of the spinal fusion cage is linearly adjusted according to a spacing between vertebral bodies of a patient, such that the surgery may be performed at the optimal height according to spinal conditions of the patient.

In addition, since the cage is inserted at the lowest height, it is possible to reduce the burden of the manufacture to separately produce the existing test inserts in accordance with a proper spacing between vertebral bodies, and it is possible to save trouble of securing an insertion space while sequentially inserting a plurality of test inserts on the doctor.

BRIEF DESCRIPTION OF DRAWINGS

The above and other objects, features and other advantages of the present invention will be more clearly understood from the following detailed description taken in conjunction with the accompanying drawings, in which.

MODE FOR CARRYING OUT INVENTION

Figure 1:
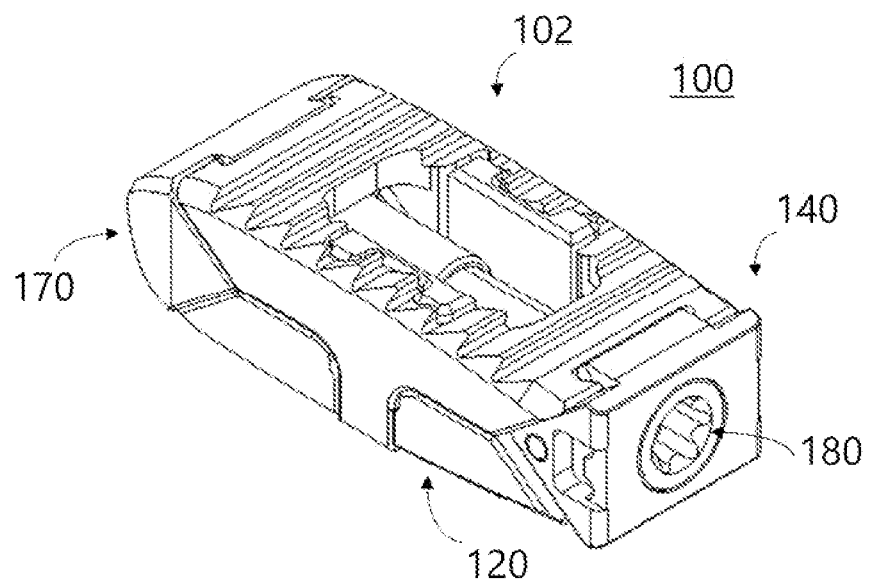
FIG. 1 is a perspective view of a spinal fusion cage according to Embodiment 1 of the present invention with being the lowest height.
Figure 2:
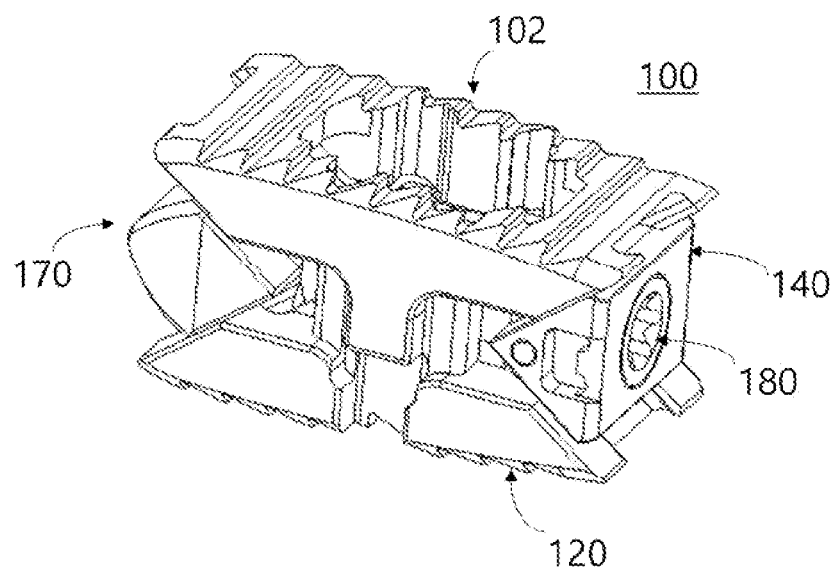
FIG. 2 is a perspective view of the spinal fusion cage shown in FIG. 1 with being the highest height.
Figure 3:
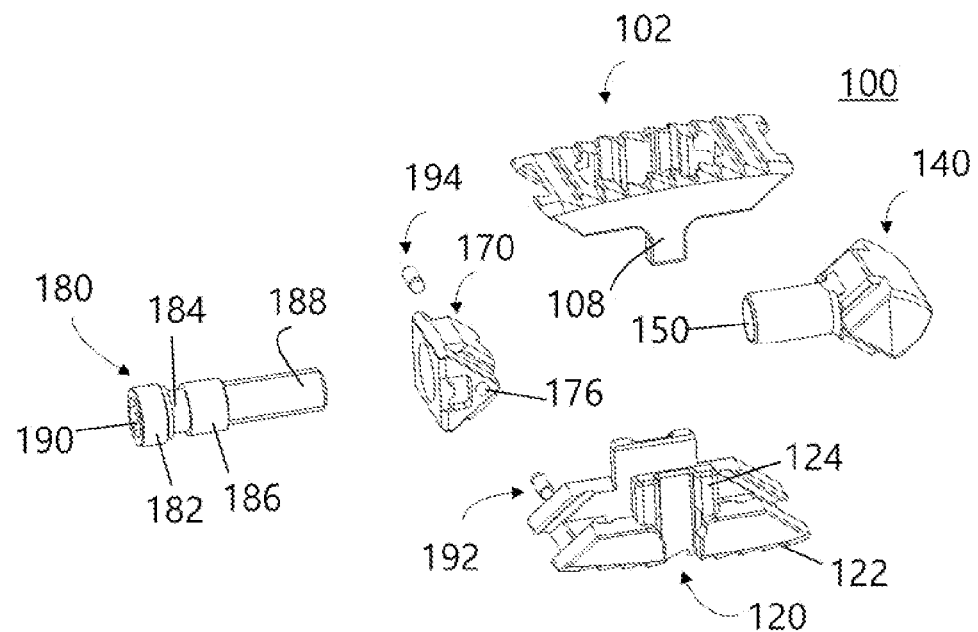
FIG. 3 is an exploded perspective view of the spinal fusion cage shown in FIG. 1.
Figure 4:
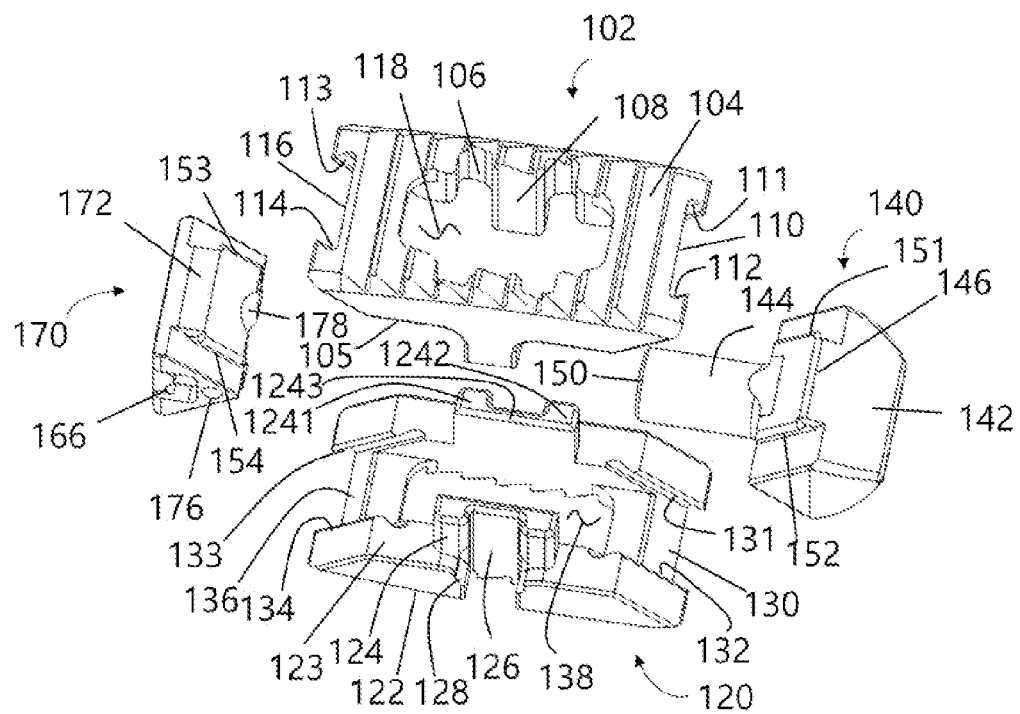
FIG. 4 is an exploded perspective view of the spinal fusion cage shown in FIG. 1 as seen from the top, except for an adjusting member.
Figure 5:
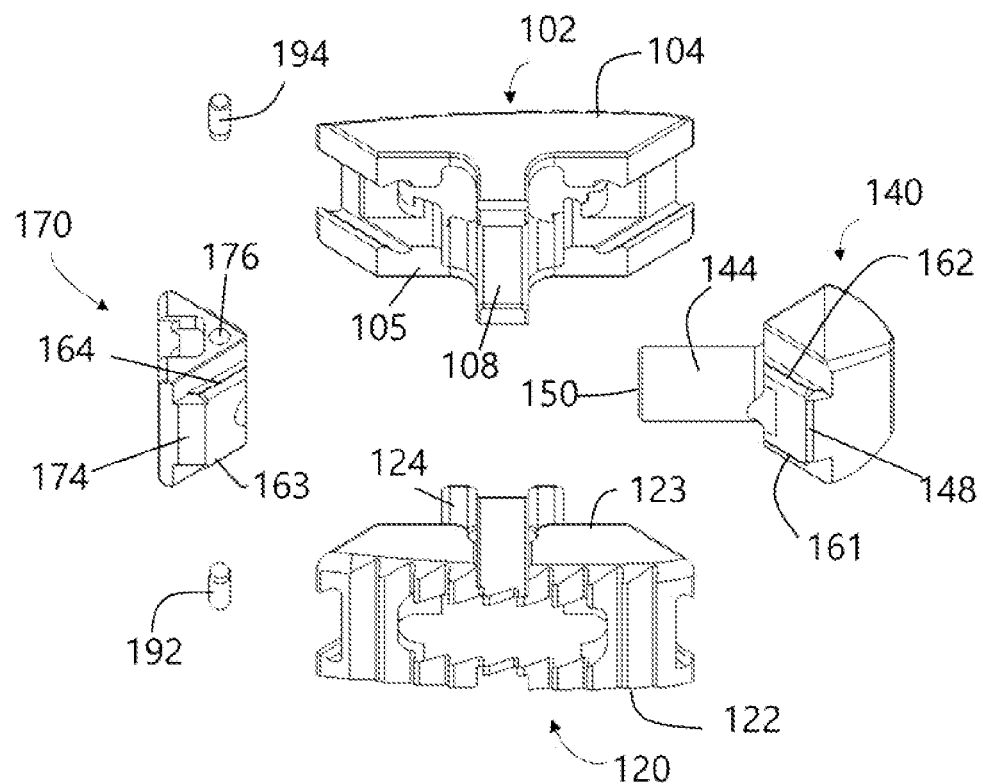
FIG. 5 is an exploded perspective view of the spinal fusion cage shown in FIG. 1 as seen from the bottom, except for the adjusting member.
Figure 6:
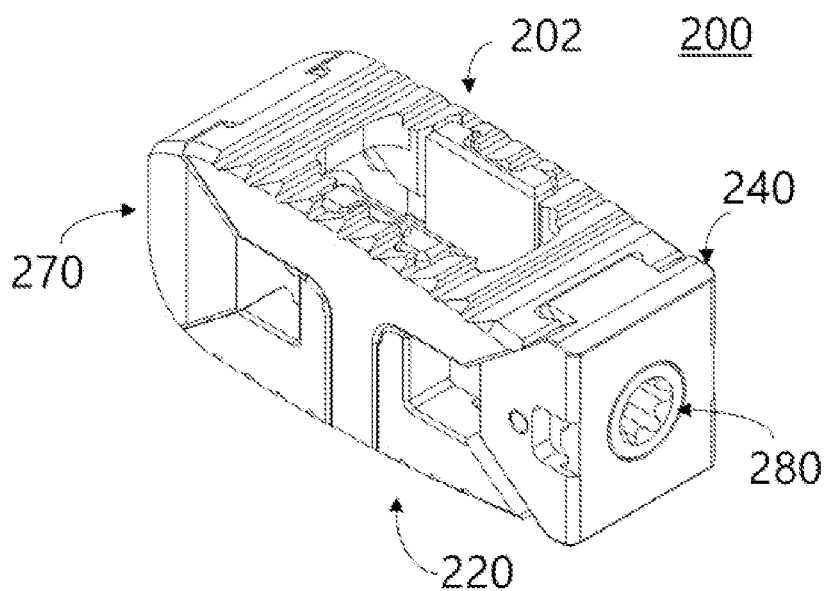
FIG. 6 is a perspective view of a spinal fusion cage according to Embodiment 2 of the present invention with being the lowest height.
Figure 7:
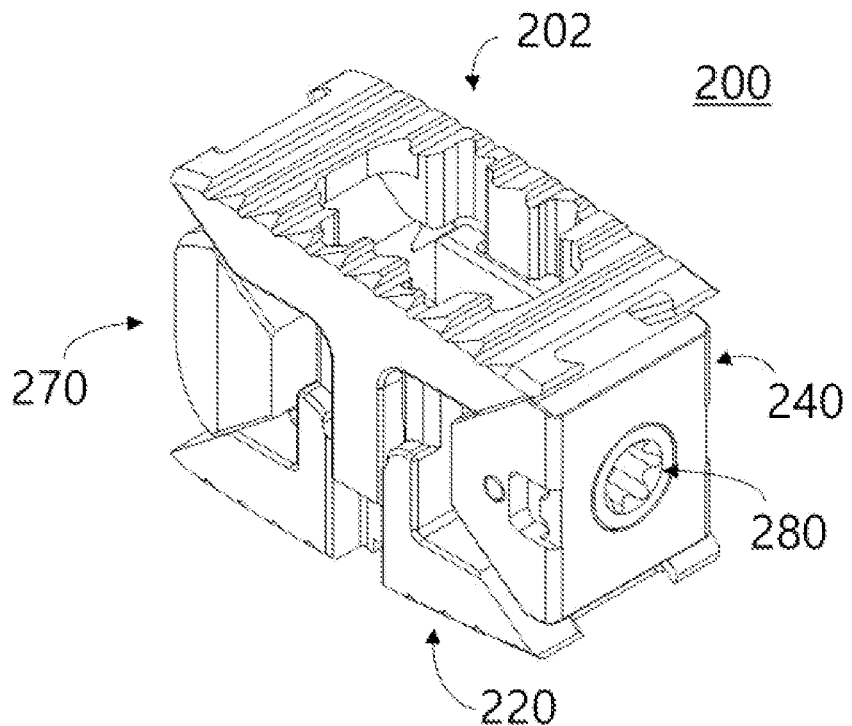
FIG. 7 is a perspective view of the spinal fusion cage shown in FIG. 6 with being the highest height.
Figure 8:
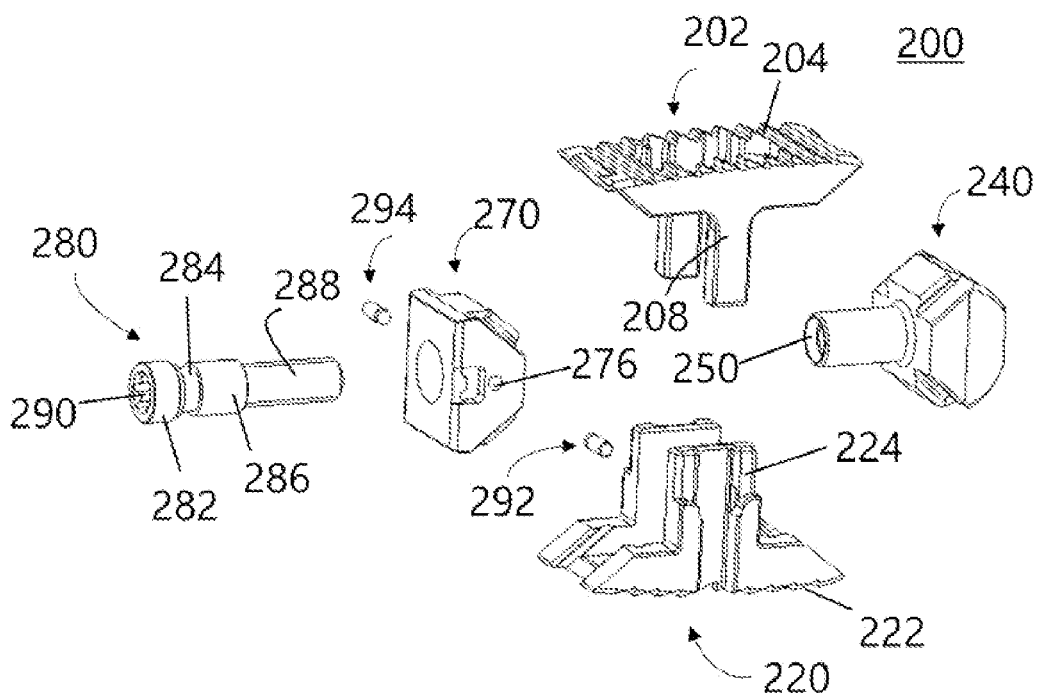
FIG. 8 is an exploded perspective view of the spinal fusion cage shown in FIG. 6.
Figure 9:
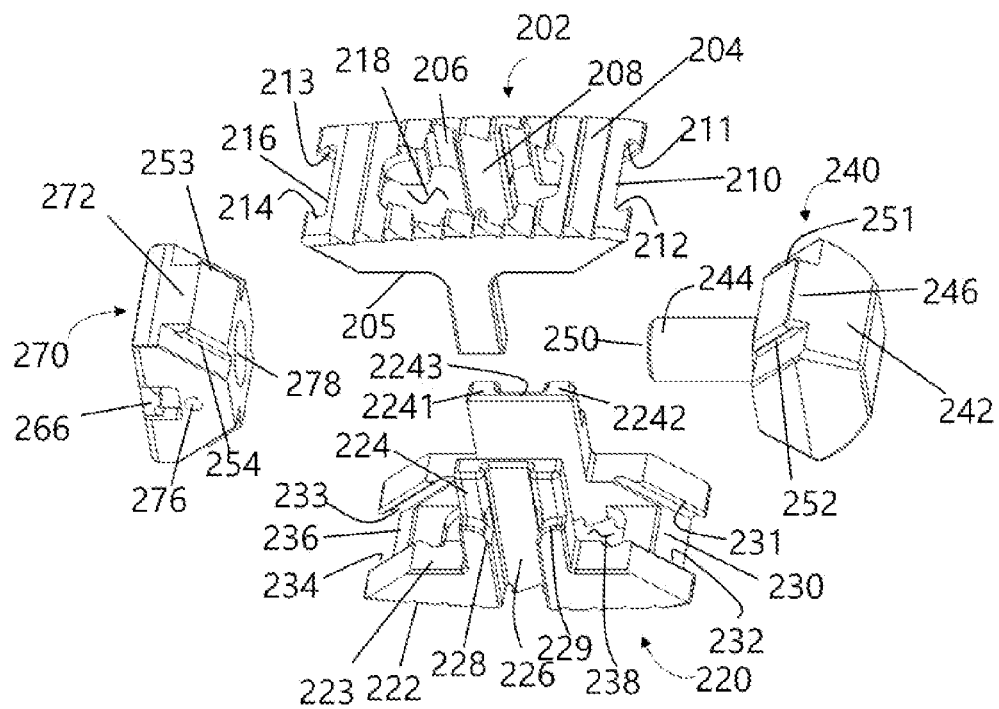
FIG. 9 is an exploded perspective view of the spinal fusion cage shown in FIG. 6 as seen from the top, except for an adjusting member.
Figure 10:
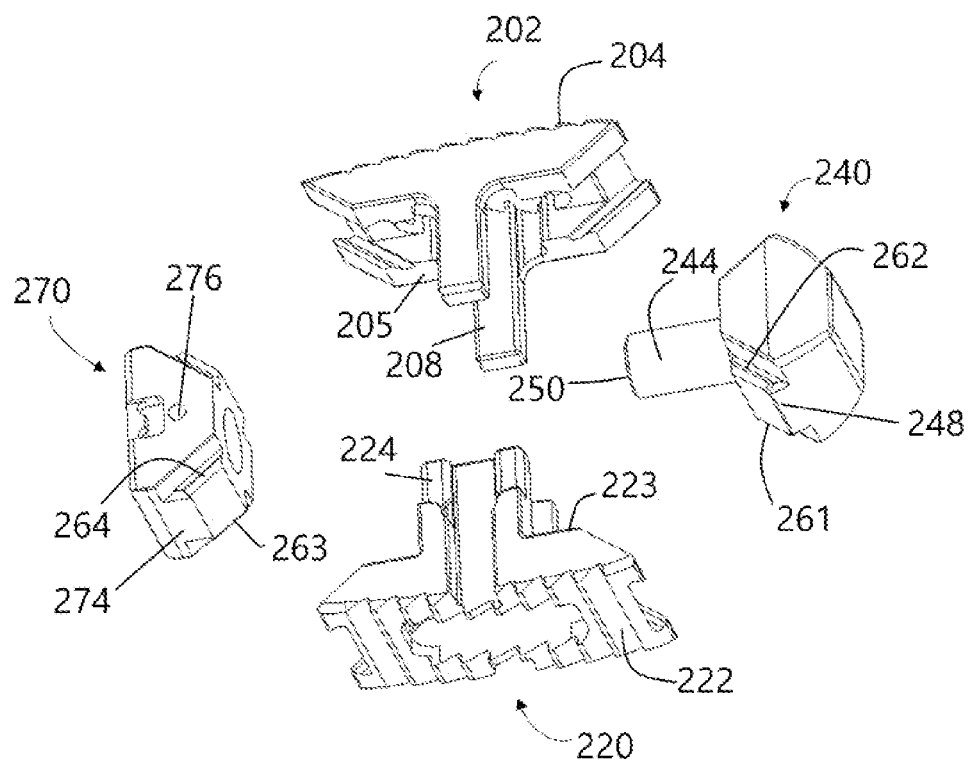
FIG. 10 is an exploded perspective view of the spinal fusion cage shown in FIG. 6 as seen from the bottom, except for the adjusting member.
Figure 11:
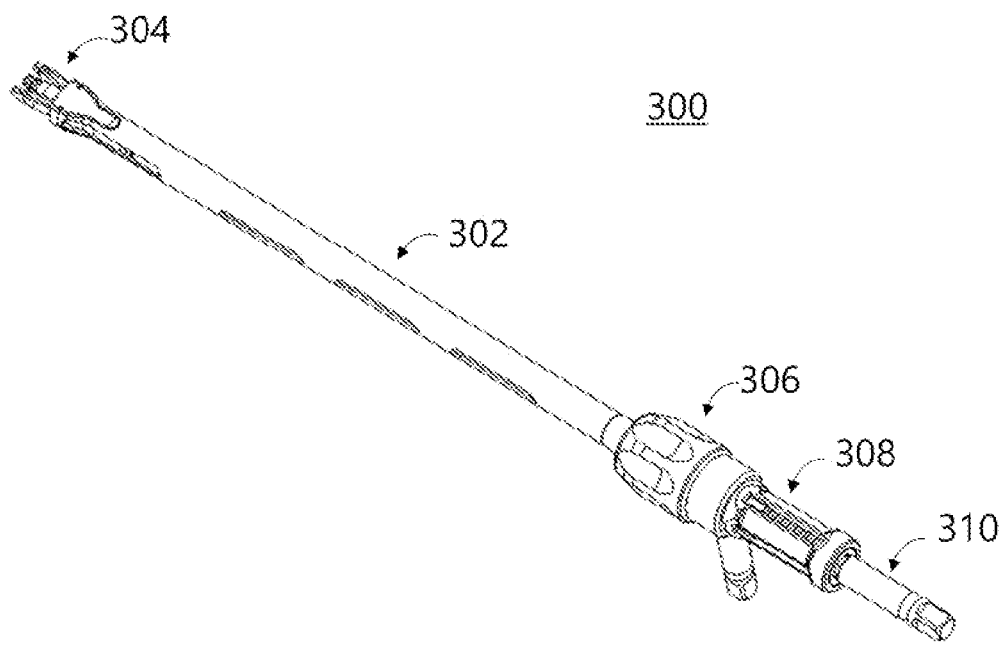
FIG. 11 is a perspective view of a cage holder according to an embodiment of the present invention.
Figure 12:
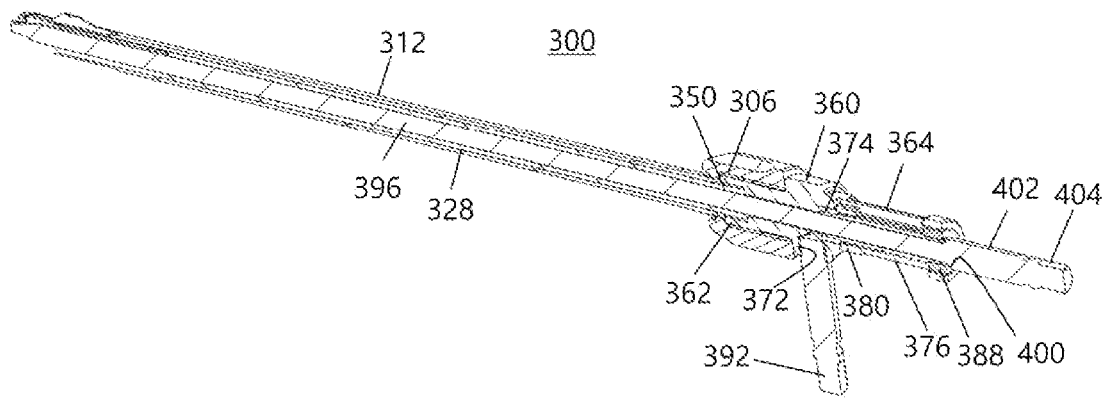
FIG. 12 is a perspective view in cross-section of the cage holder shown in FIG. 11.

Hereinafter, the present invention will be described in detail with reference to the accompanying drawings. In denoting reference numerals to constitutional elements of respective drawings, it should be noted that the same elements will be denoted by the same reference numerals although they are illustrated in different drawings. In the embodiments of the present invention, the publicly known functions and configurations that are judged to be able to make the purport of the present invention unnecessarily obscure will not be described.

FIGS. 1 to 5 illustrate a spinal fusion cage 100 according to Embodiment 1 of the present invention, and FIGS. 6 to 10 illustrate a spinal fusion cage 200 according to Embodiment 2 of the present invention. Hereinafter, the same components of Embodiment 1 and Embodiment 2 will be described together, and then differences between Embodiment 1 and Embodiment 2 will be described, respectively.

The spinal fusion cages 100, 200 according to Embodiments 1, 2 will be described with reference to FIGS. 1 to 5, and 6 to 10. The spinal fusion cages 100, 200 may include: First endplates 102, 202 and second endplates 120, 220 which are disposed vertically to face each other; distal moving blocks 140, 240 and proximal moving blocks 170, 270 which are disposed between the first endplates 102, 202 and the second endplates 120, 220 to move according to a distance between the first endplates 102, 202 and the second endplates 120, 220; and adjusting members 180, 280 which are connected to the distal moving blocks 140, 240 by passing through the proximal moving blocks 170, 270.

The first endplates 102, 202 and the second endplates 120, 220 have first plate portions 104, 204 and second plate portions 122, 222 configured to abut vertebral bodies. The first plate portions 104, 204 and the second plate portions 122, 222 may have teeth formed thereon to prevent the vertebral bodies from separating from each other. In addition, first windows 118, 218, and second windows 138, 238 for inserting bone grafts are formed at central portions of the first plate portions 104, 204 and the second plate portions 122, 222, respectively.

First plate rails 111, 211, second plate rails 112, 212, third plate rails 113, 213, and fourth plate rails 114, 214 are formed on both sides of the first plate portions 104, 204 in a longitudinal direction. The first plate rails 111, 211 and the second plate rails 112, 212 are located to face each other in a distal direction, and first plate recesses 110, 210 are formed between these rails. The third plate rails 113, 213 and the fourth plate rails 114, 214 are located to face each other in a proximal direction, and second plate recesses 116, 216 are formed between these rails. All the first plate rails 111, 211, the second plate rails 112, 212, the third plate rails 113, 213, and the fourth plate rails 114, 214 are formed in the surfaces of the first plate portions 104, 204 slantly extending upward in a thickness direction from ends toward the center of the first plate portions 104, 204 with being close to each other.

Similarly, fifth plate rails 131, 231, sixth plate rails 132, 232, seventh plate rails 133, 233, and eighth plate rails 134, 234 are formed on both sides of the second plate portions 122, 222 in the longitudinal direction. The fifth plate rails 131, 231 and the sixth plate rails 132, 232 are disposed to face each other in the distal direction, and third plate recesses 130, 230 are formed between these rails. In addition, the seventh plate rails 133, 233 and the eighth plate rails 134, 234 are located to face each other in the proximal direction, and fourth plate recesses 136, 236 are formed between these rails. All the fifth plate rails 131, 231, the sixth plate rails 132, 232, the seventh plate rails 133, 233, and the eighth plate rails 134, 234 are formed in the surface of the second plate portions 122, 222 slantly extending upward in the thickness direction from ends toward the center of the second plate portions 122, 222 with being close to each other.

The distal moving blocks 140, 240 have insertion portions 142, 242 formed therein by protruding in a streamlined shape so as to be easily inserted between the vertebral bodies in the proximal direction. In addition, the distal moving blocks 140, 240 have connecting rods 144, 244 formed therein by elongating in the distal direction, and connecting threaded holes 150, 250 having a thread are formed inside the connecting rods 144, 244. Further, the distal moving blocks 140, 240 have first block projections 146, 246 formed thereon so as to correspond to the first plate recesses 110, 210 of the first endplates 102, 202, and second block projections 148, 248 formed thereon so as to correspond to the third plate recesses 130, 230 of the second endplates 120, 220. First block rails 151, 251 and second block rails 152, 252 corresponding to the first plate rails 111, 211 and the second plate rails 112, 212 are formed around the first block projections 146, 246. Fifth block rails 151, 251 and sixth block rails 162, 262 corresponding to the fifth plate rails 131, 231 and the sixth plate rails 132, 232 are formed around the second block projections 148, 248.

The proximal moving blocks 170, 270 have through holes 178, 278 formed therein to rotatably support the adjusting members 180, 280. In addition, the proximal moving blocks 170, 270 have third block projections 172, 272 formed thereon so as to correspond to the second plate recesses 116, 216 of the first endplates 102, 202, and fourth block projections 174, 274 formed thereon so as to correspond to the fourth plate recesses 136, 236 of the second endplates 120, 220. Third block rails 153, 253 and fourth block rails 154, 254 corresponding to the third plate rails 113, 213 and the fourth plate rails 114, 214 are formed around the third block projections 172, 272. Seventh block rails 163, 263 and eighth block rails 164, 264 corresponding to the seventh plate rails 133, 233 and the eighth plate rails 134, 234 are formed around the fourth block projections 174, 274. In addition, fixing pin holes 176, 276, into which fixing pins 192, 194; 292, 294 are inserted, are formed on sides of the proximal moving blocks 170, 270. Further, engagement portions 166, 266 are formed on the sides of the proximal moving blocks 170, 270 to grip the spinal fusion cages 100, 200 by a tool.

The distal moving blocks 140, 240 and the proximal moving blocks 170, 270 have a substantially wedge shape, and are configured to move the first endplates 102, 202 and the second endplates 120, 220 by pressing up or down.

The adjusting members 180, 280 may have a shape of a substantially bolt. That is, the adjusting members 180, 280 have heads 182, 282 and adjusting threaded portions 188, 288. The heads 182, 282 are seated in openings formed in the through holes 178, 278 in the proximal direction thereof, and the adjusting threaded portions 188, 288 pass through the through holes 178, 278, and are screwed to the threaded holes 150, 250 of the connecting rods 144, 244. Tool seats 190, 290 are formed in the heads 182, 282, which may be connected with a tool (not shown). In addition, support portions 186, 286 are located between the heads 182, 282 and the through holes 178, 278, and are rotatably supported by inner wall surfaces of the through holes 178, 278 while abutting the same. In addition, pin seats 184, 284 are formed around the support portions 186, 286 such that end portions of the fixing pins 192, 194; 292, 294 inserted through the pin holes 176, 276 of the proximal moving blocks 170, 270 are seated. As a result, the adjusting members 180, 280 can be rotated in position.

A pair of columns 108, 208 is formed on both sides of the first plate portions 104, 204 in the thickness direction, that is, in a direction toward the second endplates 120, 220. Further, receiving recesses 106, 206, in which extension walls 124, 224 can be received as described below, are formed around the columns 108, 208. In addition, a pair of extension walls 124, 224 are formed on both sides of the second endplates 120, 220 in the thickness direction, that is, in the direction toward the first endplates 102, 202, and recesses 126, 226, into which the columns 108, 208 can be inserted and guided, are formed inside of the extension walls 124, 224. As a result, when the columns 108, 208 are inserted into the recesses 126, 226 and move vertically, movements of the first endplates 102, 202 and the second endplates 120, 220 in directions in which they are close to or spaced apart from each other are blocked.

In addition, the extension walls 124, 224 includes first walls 1241, 2241 and second walls 1242, 2242 which are located at a front end and a rear end of the columns 108, 208 in the longitudinal direction of the second endplates 120, 220, and third walls 1243, 2243 which connect the first walls 1241, 2241 and the second walls 1242, 2242 to form the recesses 126, 226 into which the columns 108, 208 are inserted. That is, the extension walls 124, 224 are formed to surround the columns 108, 208 while having a substantially U shape when viewing from the top.

The first walls 1241, 2241 and the second walls 1242, 2242 are formed so as to have thicknesses smaller than a value of excluding widthwise lengths of the second windows 138, 238 from widthwise lengths of the second plate portions 122, 222. The reason is that the first walls 1241, 2241 and the second walls 1242, 2242 are inserted into the receiving recesses 106, 206 of the first endplates 102, 202. In addition, the columns 108, 208 may be formed so as to have widthwise thicknesses greater than ¼ times and smaller than ½ times of a value of excluding the widthwise lengths of the first windows 118, 218 from the widthwise lengths of the first plate portions 104, 204. The reason is that the columns 108, 208 are thickened by depths of the recesses 126, 226 into which the columns 108, 208 are inserted.

In addition, guide grooves 128, 228 may be formed in the first walls 1241, 2241 and the second walls 1242, 2242 to guide the columns 108, 208 to be inserted into the recesses 126, 226. The reason is that the thicknesses of the columns 108, 208 are larger than the thicknesses of the first walls 1241, 2241 and the second walls 1242, 2242.

In addition, the spinal fusion cage 100 of Embodiment 1 and the spinal fusion cage 200 of Embodiment 2 have different positions relative to the first endplates 102, 202 and the second endplates 120, 220 at the lowest height.

The spinal fusion cage 100 of Embodiment 1 is formed so that a first bottom surface 105 of the first endplate 102 abuts a second bottom surface 123 of the second endplate 120 when it is at its lowest state.

On the other hand, the spinal fusion cage 200 of Embodiment 2 is formed so that a first bottom surface 205 of the first endplate 202 abuts stoppers 229 formed on the first wall 2241 and the second wall 2242 of the second endplate 220 when it is at its lowest state. The stopper 229 protrudes from the first wall 2241 and the second wall 2242 so as to abut around the receiving recess 206 of the first bottom surface 205 of the first endplate 202.

As a result, when the spinal fusion cage 200 of Embodiment 2 is at its lowest state, the first bottom surface 205 of the first endplate 202 and the second bottom surface 223 of the second endplate 220 are spaced apart from each other.

Like the spinal fusion cage 200 of Embodiment 2, when the height thereof in the lowest state is higher than that of the spinal fusion cage 100 of Embodiment 1, there is a limitation in the length of the spinal fusion cage 200 to be inserted into the vertebral bodies, and the proximal moving block 270 and a longitudinal length of the spinal fusion cage 200 of the distal moving block 240 is not changed. Therefore, in order to maintain a driving force of the adjusting member 280 in the same level as that of Embodiment 1, the first to eighth block rails and inclination degrees of the first to eighth plate rails should be the same as those of the spinal fusion cage 100 of Embodiment 1. Therefore, the first bottom surface 205 of the first endplate 202 and the second bottom surface 223 of the second endplate 220 need to be spaced apart from each other, and the spinal fusion cage of Embodiment 2 further includes the stopper 229.

The spinal fusion cages 100, 200 are configured as described above, and by inserting a tool such as a driver into tool grooves 190, 290 and rotating it in one direction, it is possible to perform movements in which the proximal moving blocks 170, 270 and the distal moving block 140 are close to each other, and consequently, the first endplates 102, 202 and the second endplates 120, 220 are spaced apart from each other. Similarly, by inserting the tool and rotating in the other direction, it is possible to perform the movement in which the proximal moving blocks 170, 270 and the distal moving blocks 140, 240 are spaced apart from each other, and consequently, a distance between the first endplates 102, 202 and the second endplates 120, 220 is decreased.

Next, a cage holder according to an embodiment of the present invention will be described with reference to FIGS. 11 to 25.

Specifically, a cage holder 300 according to the embodiment of the present invention will be described with reference to FIGS. 11 to 24.

US2017-02580605A discloses a holder 400 (hereinafter, not illustrated) for a height adjustable cage as illustrated in FIGS. 26 to 29. US2017-02580605A uses a method in which, while a plurality of arms 402 are inserted into or protrude from a sleeve 410, protrusions 404 formed on ends of the arms 402 are mounted in grooves 320 of a cage 300 to fix the cage 300. However, such a method has a problem that, since the arm 402 is extended by an elasticity thereof, there is a high possibility that the holder 400 may not be separated with being coupled with an implant 302 due to repeated use or obstruction of surrounding muscles at the surgical site.

In contrast, the cage holder 300 may be engaged with the spinal fusion cage to insert the spinal fusion cage between the vertebral bodies at the lowest height, and may be reliably separated from the spinal fusion cage after the surgery. Moreover, the cage holder 300 has a characteristic capable of visually indicating an amount of change in the height of the spinal fusion cage.

The cage holder 300 includes: a main body 302; a holding body 304 which is inserted into the main body 302 to relatively move with respect to the main body 302, and has a pair of end effectors 344 and 346 that protrude outwardly from one end of the main body 302; a fastener 308 integrally formed with the holding body 304; and a knob 306 mounted on the other end of the main body 302 and movably coupled to the fastener 308 in the longitudinal direction of the main body 302.

The end effectors 344 and 346 are formed at ends of legs 330 and 332 that branch out from one end of the holding body 304, and a guide unit may be formed at the one end of the main body 302 and the legs 330 and 332 to forcibly guide the legs 330 and 332.

In addition, a driver 310 may be inserted through insides of the fastener 308 and the holding body 304, and the fastener 308 may further include an indication device capable of indicating an amount of rotation of the driver by converting it into an amount of change in a length thereof.

Each of or both of the guide unit and the indication device may be included in the cage holder 300.

Figure 16:
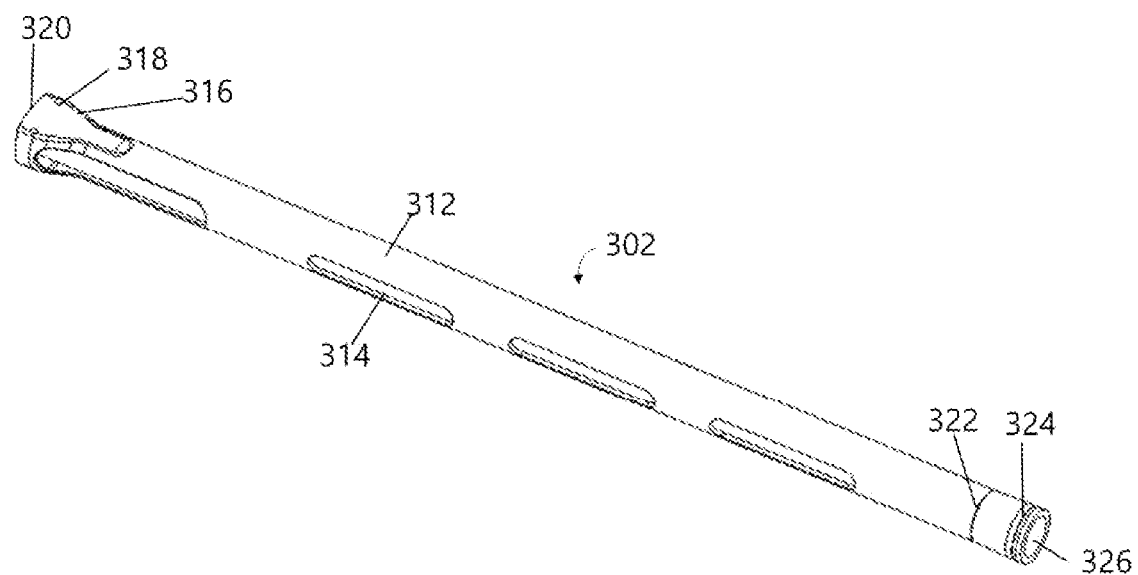
FIG. 16 is a perspective view of a main body.

As illustrated in FIG. 16, the main body 302 includes a main body tube 312 having a main body hole 326 formed therein, and one or more cleaning holes 314 disposed in length direction thereof to facilitate cleaning. The main body tube 312 has an opening 320 formed in one end thereof to communicate with the main body hole 326, and the end effectors 344 and 346 that protrude outwardly through the opening 320.

When viewing the main body 302 from the top, an end portion of the opening 320 is formed in a substantially straight line, but may be concavely or convexly formed in accordance with the shape of the proximal portion of the spinal fusion cage.

An extension portion 316 is disposed on one side of the main body tube 312. The expansion part 316 is enlarged in a width direction (consistent with the width direction of the cage) from the main body tube 312, so that the end effectors 344 and 346 formed at the ends of the legs 330 and 332 are extended in the width direction.

The guide unit may be disposed on the extension portion 316 side, and may include guide sections longitudinally formed in the legs 330 and 332, and fixing guides disposed in the main body 302 and inserted into the guide sections.

In the embodiment of the present invention, the guide sections are formed as guide slots 340 and 342 which are elongated in a longitudinal direction of the legs 330 and 332 with vertically penetrating the same, and the fixing guides are guide pins 406 and 408 which are fixed to the main body 302 by passing through the guide slots 340 and 342. The main body tube 312 has a guide pin hole 318 formed in one end thereof, into which the guide pins 406 and 408 are inserted to be installed.

A fitting groove 324 is formed in the other end of the main body tube 312, to which the knob 306 is fitted. In addition, as illustrated in FIG. 16, a locking jaw 322 is formed at the other end of the main body tube 312 far away from the fitting groove 324, which serves to prevent the knob 306 from being removed.

Figure 17:
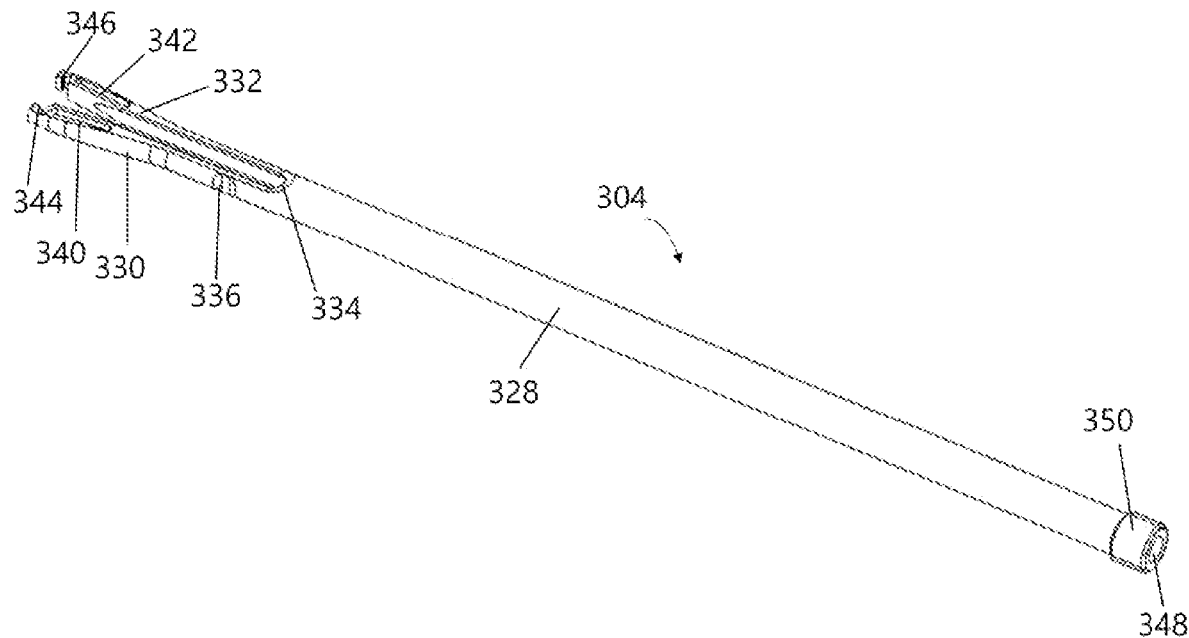
FIG. 17 is a perspective view of a holding body.
Figure 18:
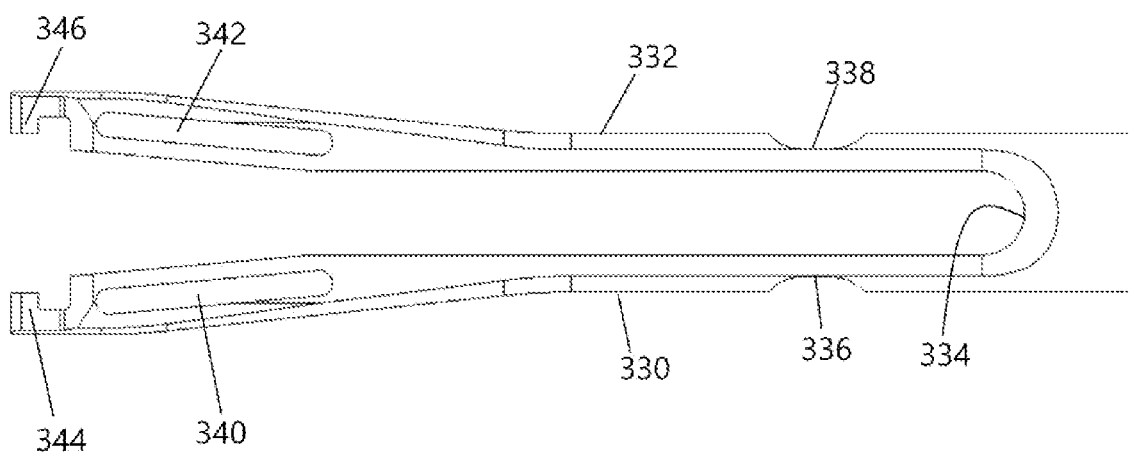
FIG. 18 is a partially enlarged plan view of the holding body shown in FIG. 16.

As illustrated in FIGS. 17 and 18, the holding body 304 has a holding body tube 328 inserted into the main body 302, and one end thereof forms two legs 330 and 332 that branch out from a branch point 334. The legs 330 and 332 have bending notches 336 and 338 formed on outer surfaces thereof, thereby serving to increase an amount of bending.

The end effectors 344 and 346 are disposed at the ends of the legs 330 and 332 to grip the cage. In addition, the guide slots 340 and 342 are formed in the legs 330 and 332 as described above.

Figure 19:
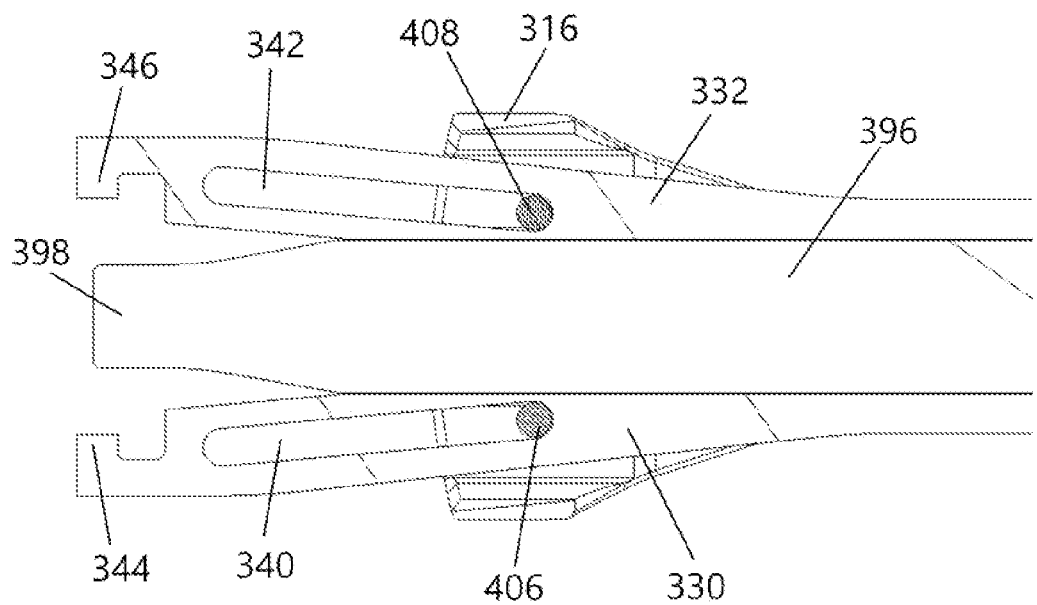
FIG. 19 is a plan view of the cage holder on an end effector side shown in FIG. 11 in the exploded state.

FIG. 19 illustrates a state in which the legs 330 and 332 are arranged in the extension portion 316 of the main body 302. In this state, guide pins 406 and 408 are inserted into the guide slots 340 and 342 formed in the legs 330 and 332. Therefore, when the holding body 304 moves toward the one end of the main body 302 in the longitudinal direction thereof to increase a protruded length of the end effectors 344 and 346, an interval between the pair of end effectors 344 and 346 is enlarged. On the other hand, when the holding body 304 moves back from the one end of the main body 302 in the longitudinal direction thereof to decrease the protruded length of the end effectors 344 and 346, the interval between the pair of end effectors 344 and 346 is narrowed. That is, it is possible to forcibly enlarge or reduce the legs 330 and 332 by the above-described guide pins 406 and 408 and the guide slots 340 and 342.

A coupling portion 350 is formed at the other end of the holding body 304 to be fixed to the fastener 308. The coupling portion 350 may be fixed to the holding body 304 by a method using well-known techniques such as screwing by threads, welding, fixing using pins, epoxy bonding and the like.

Figure 20:
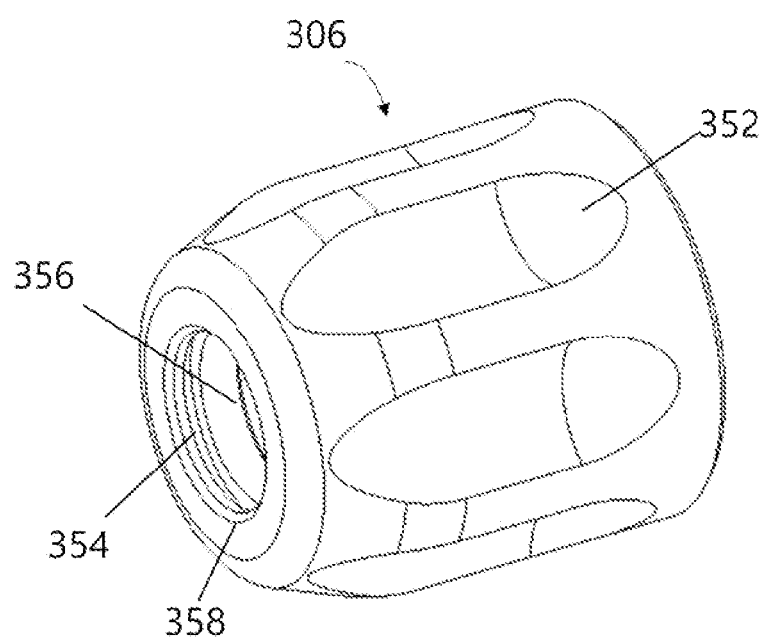
FIG. 20 is a perspective view of a knob.

As illustrated in FIG. 20, the knob 306 serves to apply a rotational force to move the holding body 304 with respect to the main body 302. To this end, the knob 306 include: a knob body 352 having irregularities formed on an outer circumference thereof so as to facilitate gripping by hand; a fitting step 354 formed on an inner surface thereof to be fitted to the fitting groove 324 of the main body 302; and a knob thread 356 formed on the inner surface thereof to be screwed with a fastener thread 362 formed on the fastener 308 to be described below. The knob 306 has a knob hole 358 formed therein to have a tube shape as a whole.

Figure 21:
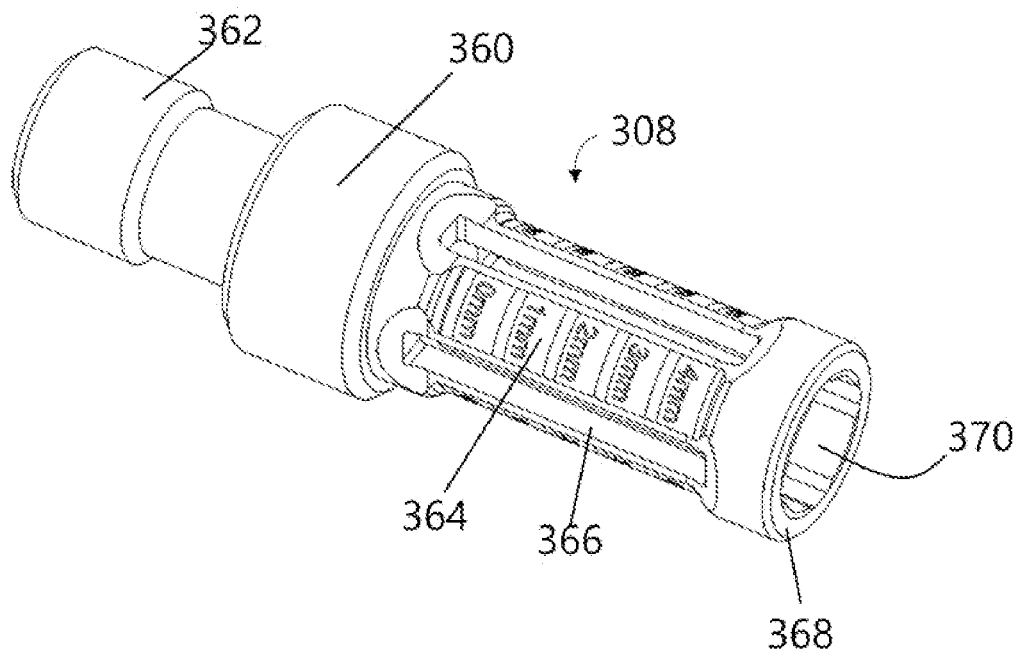
FIG. 21 is a perspective view of a fastener.
Figure 22:
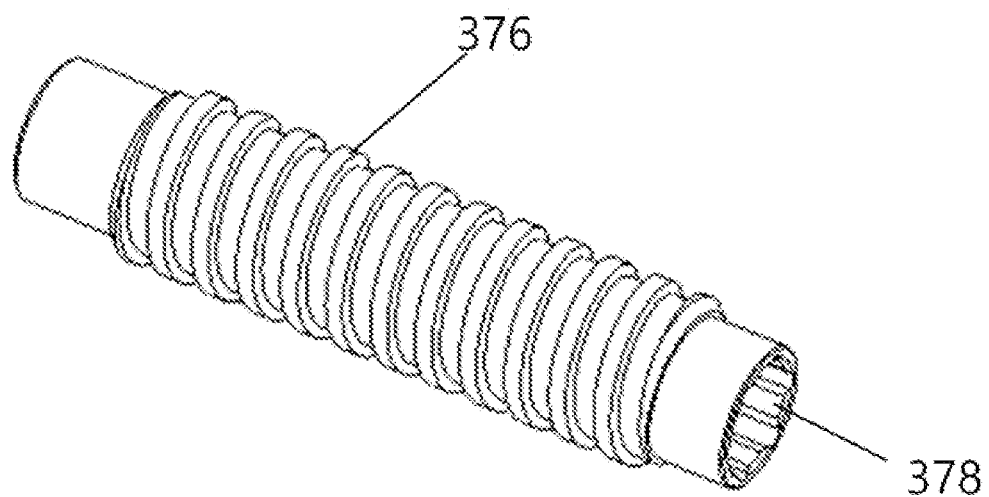
FIG. 22 is a perspective view of the movement conversion rod.
Figure 23:
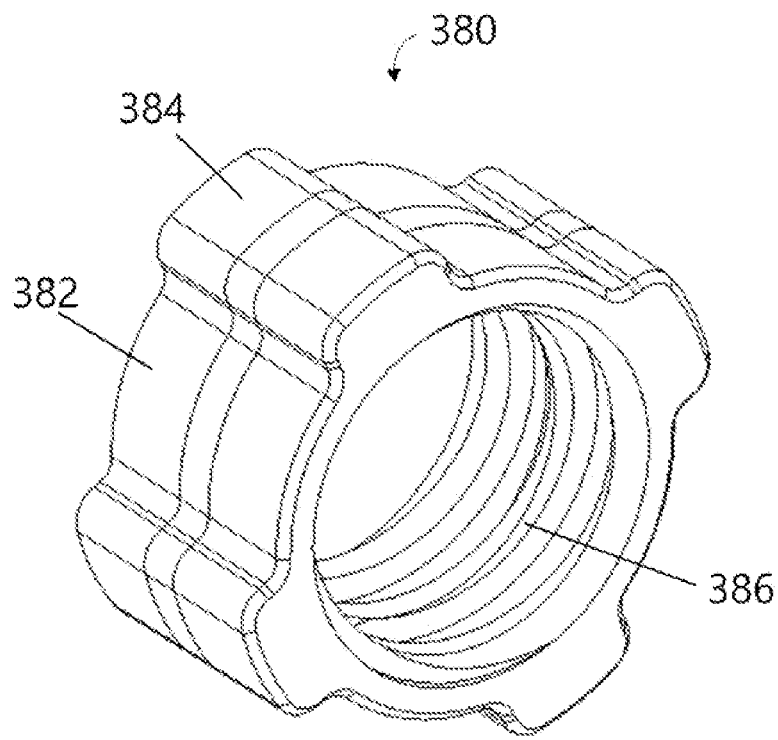
FIG. 23 is a perspective view of a moving indicator.
Figure 24:
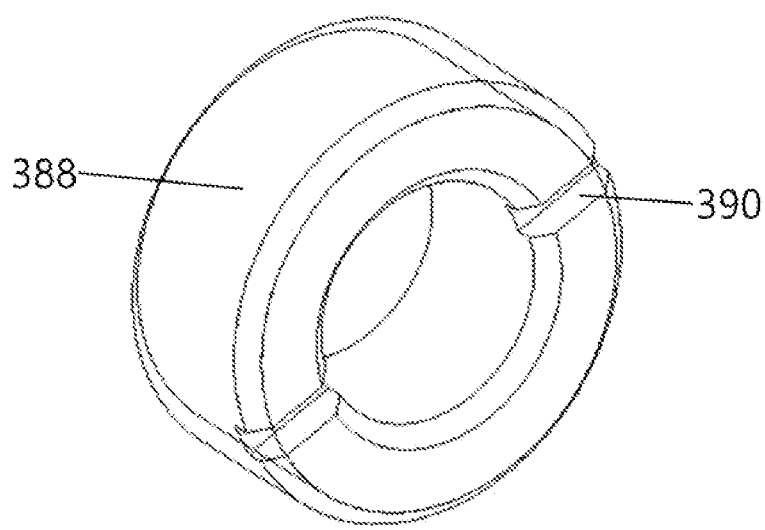
FIG. 24 is a perspective view of a retainer.

As illustrated in FIG. 21, the fastener 308 includes a fastener body 360 having the fastener thread 362 formed at one end thereof, and a marking portion 364 formed at the other end thereof. The marking portion 364 is a tube body communicating with the fastener hole 368 of the fastener 308, and has a plurality of marking portion slots 366 formed therein in the longitudinal direction. The marking portion 364 may have a fastener guide section 370 formed on an inner wall surface of the fastener hole 368, into which a moving indicator 380 is inserted.

In addition, the fastener 308 may have a handle coupling portion 372 formed on the outer circumference thereof, to which a handle 392 is inserted to be fixed. The handle 392 may have a connecting chuck 394 (FIG. 14) formed at one end thereof, to which an additional handle is coupled.

A scale capable of indicating a length is displayed on an outer circumference of the marking portion 364, and the height of the current cage can be indicated by a marker displayed on the moving indicator 380.

Then, a movement conversion rod 376 is inserted into the marking portion 364 through the fastener hole 368 to be rotatably supported by a rotational support ring 374. The movement conversion rod 376 has a thread formed on an outer circumference thereof, and the thread is screwed with a moving indicator threaded portion 386 formed on an inner circumference of the moving indicator 380. If a pitch of the thread formed on the movement conversion rod 376 is the same as the pitch of the thread formed on the adjusting member of the cage, a movement amount of the moving indicator 380 is small and it is difficult to visually grasp. Therefore, the thread of the movement conversion rod 376 is greater than the pitch of the thread of the adjusting member or has a plurality of threaded-lines so as to expand a lead of the adjusting member.

In addition, the moving indicator 380 has a movement indication protrusion 384 formed around a moving indicator body 382 so as to protrude from the marking portion slot 366 to be guided.

Finally, the moving indicator 380 is inserted into the marking portion 364 of the fastener 308, and a retainer 388 is fastened to prevent the moving indicator 380 from being removed. The retainer 388 is fixed to the end of the marking portion 364 using known techniques such as screwing, welding, epoxy bonding and the like. The retainer 388 may have a retainer tool groove 390 formed therein to be engaged with the tool or the like.

The driver 310 is inserted through the fastener 308 and a holding body hole 348 formed in the holding body 304. The driver 310 may have a drive tip 398 formed at one end of a shaft 396 thereof to be engaged with the adjusting member of the cage. In addition, the driver 310 may have a driver coupling portion 400 formed at the other end thereof corresponding to a driver seat 378 formed on the inner surface of the opening formed in the movement conversion rod hole 410 of the movement conversion rod 376. In addition, the driver 310 may have a driver chuck 404 formed at the other end thereof to be engaged with the handle, which is continued to the driver coupling portion 400 with the connecting rod 402 interposed therebetween.

Figure 13:
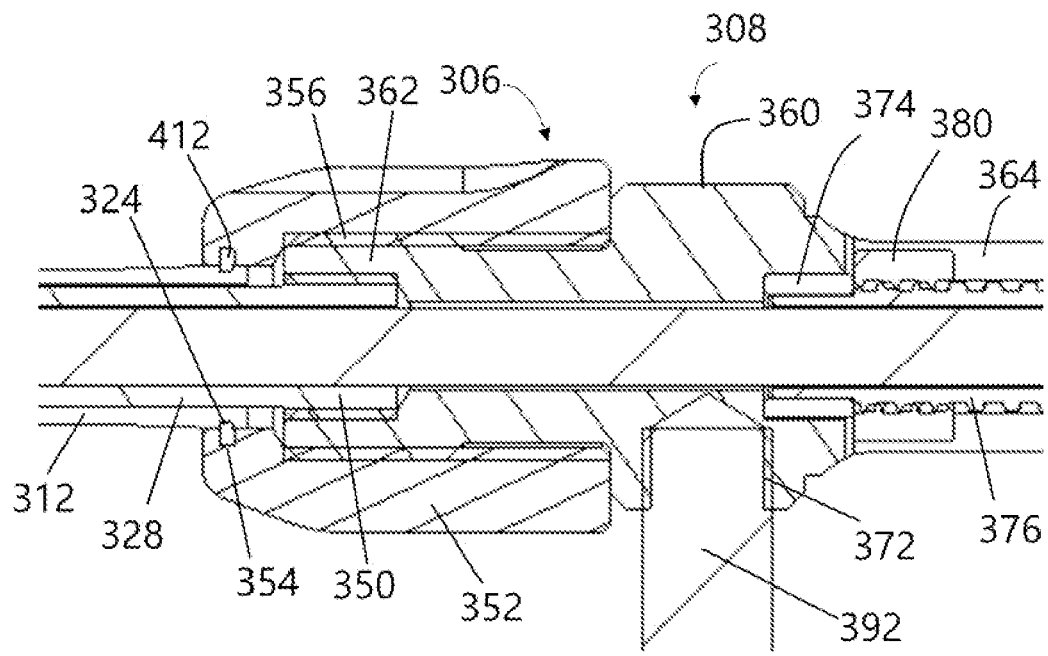
FIG. 13 is a partially enlarged cross-section of the cage holder shown in FIG. 11.

Next, a driving principle for moving the holding body 304 with respect to the main body 302 will be described with reference to FIGS. 13 and 20.

The coupling ring 412 is inserted into and fixed to the fitting groove 324 of the main body 302 and the fitting step 354 of the knob 306. Thus, the main body 302 and the knob 306 are fixed to each other, and the knob 306 is rotatable with respect to the main body 302. The coupling portion 350 of the holding body tube 328 is inserted into and fixed to the fastener 308. Accordingly, the fastener 308 and the holding body tube 328 become one body. Then, the fastener thread 362 of the fastener 308 and the knob thread 356 of the knob 306 are screwed with each other.

Accordingly, when rotating the knob 306, the knob thread 356 rotates with respect to the fastener thread 362, thereby allowing the main body 302 to be close to or be spaced apart from the fastener 308. As a result, the holding body 304 integrally formed with the fastener 308 moves forward and backward, and the legs 330 and 332 formed at one end of the holding body 304 also move forward and backward. The movement of the end effectors 344 and 346 due to the forward and backward movement of the legs 330 and 332 is as described above.

Figure 14:
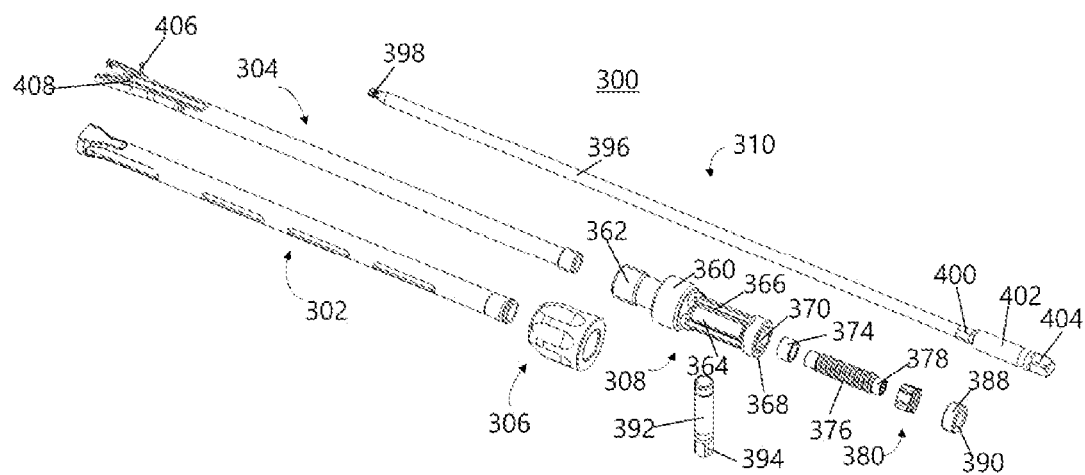
FIG. 14 is an exploded perspective view of the cage holder shown in FIG. 11.
Figure 15:
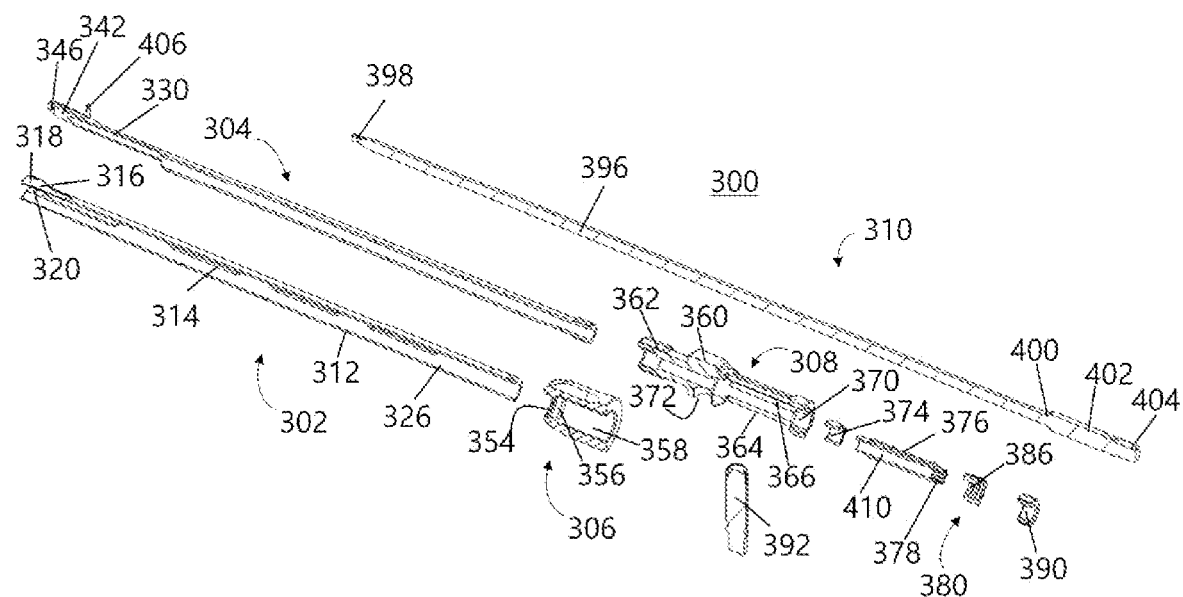
FIG. 15 is a perspective view in cross-section of the cage holder shown in FIG. 11 in an exploded state.

Next, the indication device will be described with reference to FIGS. 14 and 15. The indication device includes: The marking portion 364 connected to the fastener 308; the movement conversion rod 376 which is inserted into the marking portion 364 and has the driver seat 378 formed therein, on which the driver 310 is seated; and the moving indicator 380 which is screwed with the movement conversion rod 376 and is exposed to an outside through the marking portion slot 366 formed in the marking portion 364, so as to move along the marking portion slot 366 according to a rotation of the movement conversion rod 376 when rotating the driver 310.

When the driver 310 is inserted and rotates while the driver coupling portion 400 and the driver seat 378 are engaged to each other, the rotation of the driver 310 is transmitted to the movement conversion rod 376. Then, the moving indicator 380 screwed with the movement conversion rod 376 is moved by the rotation of the movement conversion rod 376. When the movement indication protrusion 384 of the moving indicator 380 moves at the outside along the marking portion slot 366, the height of the current cage may be determined by reading a position where the marking formed on the marking portion 364 matches the marking of the movement indication protrusion 384.

Figure 25:
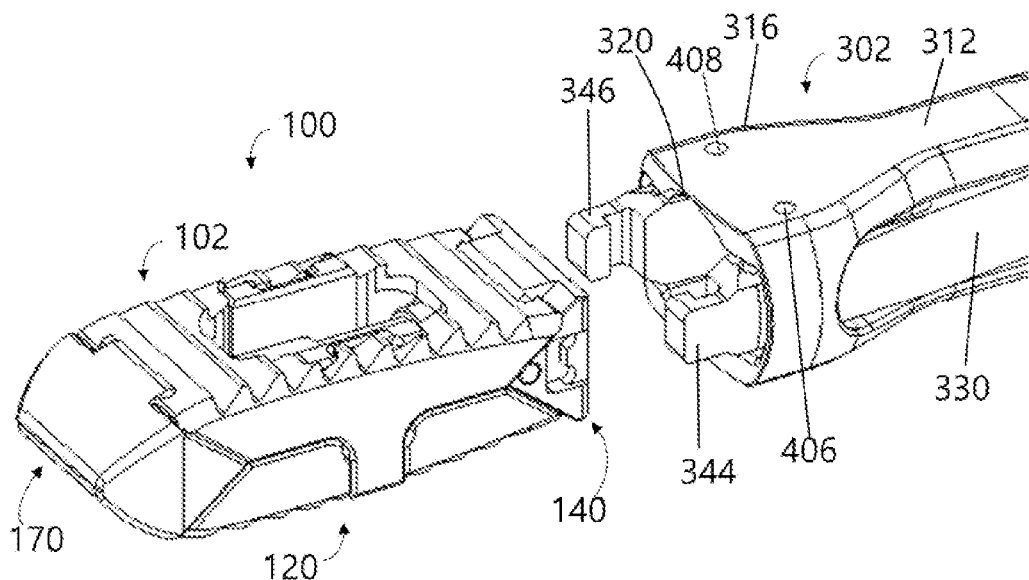
FIG. 25 is a perspective view of the spinal fusion cage with being close to the cage holder of Embodiment 1.
Figure 26:
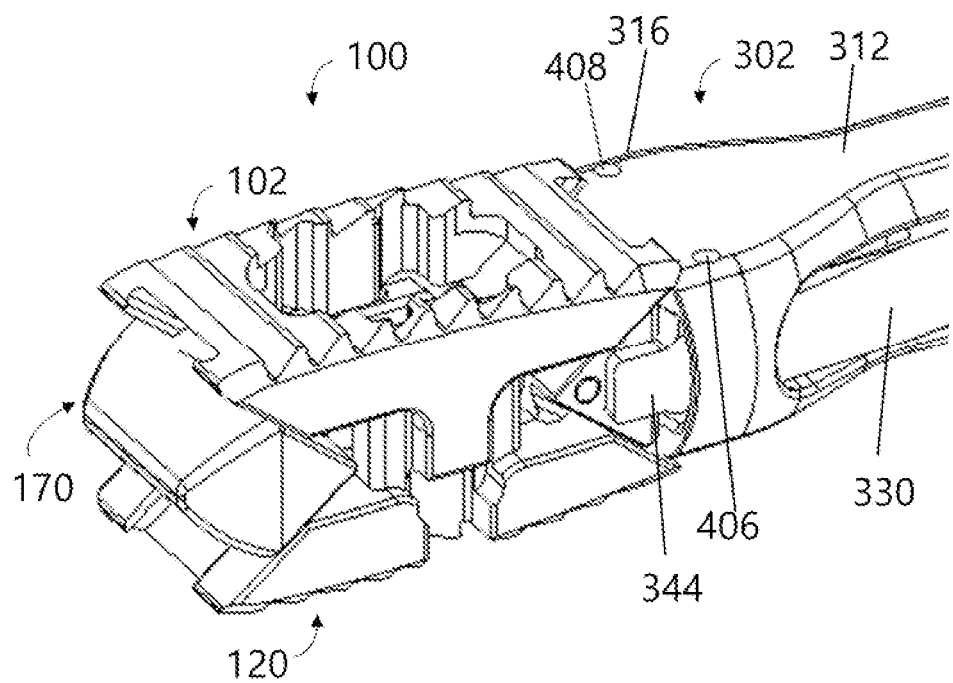
FIG. 26 is a perspective view of the spinal fusion cage of Embodiment 1 in the maximum height due to the cage holder coupled thereto.

Next, FIG. 25 illustrates a state in which the spinal fusion cage 100 and the cage holder 300 engaged with each other. The cage holder 300 is close to the cage holder 300 in the lowest height sight, thereby allowing the end effectors 344 and 346 to be located around the engagement portions 166 formed on the sides of the spinal fusion cage 100.

When rotating the knob 306 to move backward the holding body 304, the end effectors 344 and 346 are inserted into the engagement portions 166 to fix the spinal fusion cage 100. At this time, since the shape of the opening 320 corresponds to the shape of the proximal moving block 170, they can be in close contact with each other, and thus the shaking of the spinal fusion cage 100 may be prevented.

Next, the driver 310 is inserted into the cage holder 300 and the drive tip 398 of the driver 310 is engaged to the tool groove 190 of the adjusting member 180. Thereafter, when rotating the driver 310, the adjusting member 180 is rotated, and thereby allowing the proximal moving block 170 and the distal moving block 140 to be close to each other, as well as, as illustrated in FIG. 25, the first endplate 102 and the second endplate 120 are spaced apart from each other.

According to the cage holder 300 of the present invention, it is possible to insert the spinal fusion cage between adjacent vertebral bodies, and may be stably separated from the cage, thereby preventing accidents that may occur during the surgery.

In particular, since the height of the cage between the implants may be directly confirmed by eyes from the outside of the surgical area, the surgery may be accurately performed, such that it is more suitable for less experienced doctors.

While the present invention has been described with reference to the preferred embodiments, it will be understood by those skilled in the related art that various modifications and variations may be made therein without departing from the scope of the present invention as defined by the appended claims.

INDUSTRIAL APPLICABILITY

According to the present invention, cages having different heights within a certain range may be replaced by one cage, such that it is possible to reduce burdens on the stock and production, decrease the repetitive work during the surgery, thus to reduce the labor of the doctor. In addition, since the operation time is also reduced, the amount of bleeding is reduced, a recovery time of the patient may be significantly shortened, such that the spinal fusion cage of the present invention may be expected to be widely used in the related field due to the above-described advantages.

DESCRIPTION OF REFERENCE NUMERALS 100, 200: Spinal fusion cage
102, 202: First endplate
104, 204: First plate portion
105, 205: First bottom surface
106, 206: Receiving recess
108, 208: Column
110, 210: First plate recess
111, 211: First plate rail
112, 212: Second plate rail
113, 213: Third plate rail
114, 214: Fourth plate rail
116, 216: Second plate recess
118, 218: First window
120, 220: Second endplate
122, 222: Second plate portion
123, 223: Second bottom surface
124, 224: Extension wall
126, 226: Recess
128, 228: Guide groove
130, 230: Third plate recess
131, 231: Fifth plate rail
132, 232: Sixth plate rail
133, 233: Seventh plate rail
134, 234: Eighth plate rail
136, 236: Fourth plate recess
138, 38: Second window
140, 240: Distal moving block
142, 242: Insertion portion
144, 244: Connecting rod
146, 246: First block projection
148, 248: Second block projection
150, 250: Connecting threaded hole
151, 251: First block rail
152, 252: Second block rail
153, 253: Third block rail
154, 254: Fourth block rail
161, 261: Fifth block rail
162, 262: Sixth block rail
163, 263: Seventh block rail
164, 264: Eighth block rail
166, 266: Engagement portion
170, 270: Proximal moving block
172, 272: Third block projection
174, 274: Fourth block projection
176, 276: Pin hole
178, 278: Through hole
180, 280: Adjusting member
182, 282: Head
184, 284: Pin seat
186, 286: Support portion
188, 288: Adjusting threaded portion
190, 290: Tool seat
192, 194, 292, 294: Fixing pin
229: Stopper
1241, 2241: First wall
1242, 2242: Second wall
1243, 2243: Third wall
300: Cage holder
302: Main body
304: Holding body
306: Knob
308: Fastener
310: Driver
312: Main body tube
314: Cleaning hole
316: Guide unit
318: Guide pin hole
320: Opening
322: Locking jaw
324: Fitting groove
326: Main body hole
328: Holding body tube
330, 332: Leg
334: Branch point
336, 338: Bending notch
340, 342: Guide slot
344, 346: End effector
348: Holding body hole
350: Coupling portion
352: Knob body
354: Fitting step
356: Knob thread
358: Knob hole
360: Fastener body
362: Fastener thread
364: Marking portion
366: Marking portion slot
368: Fastener hole
370: Fastener guide section
372: Handle coupling portion
374: Rotational support ring
376: Movement conversion rod
378: Driver seat
380: Moving indicator
382: Moving indicator body
384: Movement indication protrusion
386: Moving indicator threaded portion
388: Retainer
390: Retainer tool groove 392: Handle
394: Connecting chuck
396: Shaft
398: Drive tip
400: Driver coupling portion
402: Connecting rod
404: Driver chuck
406, 408: Guide pin
410: Movement conversion rod hole
412: Coupling ring

What is claimed is:

1. A spinal fusion cage comprising:
a first endplate and a second endplate configured to abut adjacent vertebral bodies;
a distal moving block installed to relatively move with respect to plate inclined portions formed at one end of each of the first endplate and the second endplate;
a proximal moving block installed to relatively move with respect to plate inclined portions formed at the other end of each of the first endplate and the second endplate;
an adjusting member rotatably mounted in the proximal moving block and screwed with the distal moving block, so as to adjust a distance between the distal moving block and the proximal moving block;
a first guide unit formed in the first endplate toward the second endplate; and
a second guide unit formed in the second endplate toward the first endplate to block movements of the first endplate and the second endplate in directions in which they are close to or spaced apart from each other by sliding with the first guide unit,
wherein the first guide unit and the second guide unit are configured to support loads of the first endplate and the second endplate in a longitudinal or width direction thereof,
wherein the first guide unit comprises columns that protrude toward the second endplate, and the second guide unit comprises extension walls that extend toward the first endplate to slide with respect to the columns,
wherein the first guide unit comprises receiving recesses formed around the columns to receive the extension walls when the first endplate and the second endplate are close to each other,
wherein the extension wall comprises: a first wall and a second wall located at a front end and a rear end of the column in the longitudinal direction of the second endplate; and
a third wall which connects the first wall and the second wall to form a groove into which the column is inserted,
wherein the extension wall surrounds a part of the column as the column is inserted, and
wherein a portion of the column extending toward the second endplate has a proximal side surface, a distal side surface, a medial side surface, a lateral side surface, and a bottom surface that protrude toward the second endplate.

2. The spinal fusion cage according to claim 1, wherein the distal moving block and the proximal moving block have block sliders formed therein, and the plate inclined portions of the first and second endplates have plate sliders formed therein to slide with respect to the block sliders.

3. The spinal fusion cage according to claim 2, wherein the block slider and the plate slider have a shape of a dovetail so as to maintain a state of being engaged with each other.

4. The spinal fusion cage according to claim 1, wherein the adjusting member comprises: a threaded portion screwed to a threaded hole formed in the distal moving block at one end; and a pin seat fixed to the other end so as to be rotatable with respect to the proximal moving block,
wherein an adjusting member pin is located in the pin seat through the proximal moving block.

5. The spinal fusion cage according to claim 1, wherein the first wall and the second wall have stoppers formed thereon to abut a bottom surface of the first endplate around the receiving recess, such that the first endplate and the second endplate are spaced apart from each other at a predetermined distance in a state in which the first endplate and the second endplate are maximally close to each other.

6. The spinal fusion cage according to claim 1, wherein the first wall and the second wall comprise guide grooves formed therein to guide the column to be inserted into the recess.

7. The spinal fusion cage according to claim 1, wherein the width of the column is between ¼ and ½ times the value of the difference between the length of a first window and the length of a first plate portion.

* * * * *